United States Patent
Ziolo et al.

(10) Patent No.: US 9,855,027 B2
(45) Date of Patent: Jan. 2, 2018

(54) RETRACTOR DEVICE AND METHOD

(71) Applicant: BLACKSTONE MEDICAL, INC., Lewisville, TX (US)

(72) Inventors: Tara Ziolo, Hewitt, NJ (US); Frank Larosa, Neptune, NJ (US); John Lovell, North Bergen, NJ (US); Sergey Fedorov, Plano, TX (US)

(73) Assignee: Blackstone Medical, Inc., Lewisville, TX (US)

( * ) Notice: Subject to any disclaimer, the term of this patent is extended or adjusted under 35 U.S.C. 154(b) by 0 days.

(21) Appl. No.: 14/030,546

(22) Filed: Sep. 18, 2013

(65) Prior Publication Data

US 2014/0114139 A1 Apr. 24, 2014

Related U.S. Application Data (63) Continuation-in-part of application No. 13/659,673, filed on Oct. 24, 2012, now Pat. No. 9,693,761.

(51) Int. Cl.
*A61B 1/32* (2006.01)
*A61B 17/02* (2006.01)

(52) U.S. Cl.
CPC ........ *A61B 17/025* (2013.01); *A61B 17/0293* (2013.01); *A61B 2017/0256* (2013.01)

(58) Field of Classification Search
CPC ............ A61B 17/3423; A61B 17/0293; A61B 17/02; A61B 17/0206; A61B 1/32
USPC .................................................. 600/201–249
See application file for complete search history.

(56) References Cited

U.S. PATENT DOCUMENTS

| | | | | |
|---|---|---|---|---|
| 1,428,653 | A * | 9/1922 | Nick | 606/41 |
| 2,083,573 | A * | 6/1937 | Morgan | 600/224 |
| 2,594,086 | A * | 4/1952 | Smith | 600/228 |
| 3,965,890 | A * | 6/1976 | Gauthier | 600/215 |
| 4,130,113 | A * | 12/1978 | Graham | 600/224 |
| 4,942,700 | A | 7/1990 | Hoberman | |
| 5,024,031 | A | 6/1991 | Hoberman | |
| 5,081,983 | A * | 1/1992 | Villalta et al. | 600/224 |
| 5,125,396 | A * | 6/1992 | Ray | 600/208 |
| 5,183,032 | A * | 2/1993 | Villalta et al. | 600/224 |
| 5,377,667 | A * | 1/1995 | Patton | A61B 1/32 600/184 |
| 5,505,690 | A * | 4/1996 | Patton et al. | 600/210 |
| 5,509,893 | A * | 4/1996 | Pracas | 600/224 |
| 5,657,584 | A | 8/1997 | Hamlin | |
| 5,846,249 | A * | 12/1998 | Thompson | 606/119 |
| 5,944,658 | A * | 8/1999 | Koros et al. | 600/232 |
| 6,096,046 | A * | 8/2000 | Weiss | 606/119 |
| 6,206,828 | B1 * | 3/2001 | Wright | 600/232 |

(Continued)

OTHER PUBLICATIONS

International Search Report and Written Opinion, PCT/US2013/066628, dated Dec. 23, 2013, 10 pages.

(Continued)

*Primary Examiner* — Eduardo C Robert
*Assistant Examiner* — Michelle C Eckman
(74) *Attorney, Agent, or Firm* — Baker & McKenzie LLP (57) ABSTRACT

The present disclosure generally relates to a retractor device for retracting soft tissue to provide access to a surgical site. The retractor device includes a plurality of arms coupled to a frame and operatively coupled to a ring disposed at least partially within the frame. Related methods of using the retractor device are also described.

28 Claims, 8 Drawing Sheets

(56) References Cited

U.S. PATENT DOCUMENTS

| | | | |
|---|---|---|---|
| 6,280,379 B1* | 8/2001 | Resnick | 600/220 |
| 6,342,036 B1* | 1/2002 | Cooper et al. | 600/224 |
| 6,354,995 B1* | 3/2002 | Hoftman et al. | 600/219 |
| 6,416,468 B2* | 7/2002 | Deckman et al. | 600/231 |
| 6,440,064 B1* | 8/2002 | Rehm | 600/232 |
| 6,613,038 B2* | 9/2003 | Bonutti et al. | 604/509 |
| 6,746,396 B1* | 6/2004 | Segermark et al. | 600/233 |
| 7,182,730 B2* | 2/2007 | Fehling | 600/224 |
| 7,195,592 B2* | 3/2007 | Ravikumar et al. | 600/219 |
| 7,344,495 B2* | 3/2008 | Ravikumar et al. | 600/219 |
| 7,374,534 B2* | 5/2008 | Dalton | 600/222 |
| 7,435,219 B2* | 10/2008 | Kim | 600/233 |
| 7,491,168 B2 | 2/2009 | Raymond et al. | |
| 7,537,565 B2* | 5/2009 | Bass | 600/219 |
| 7,556,600 B2* | 7/2009 | Landry et al. | 600/233 |
| 7,594,888 B2* | 9/2009 | Raymond et al. | 600/219 |
| 7,722,570 B2* | 5/2010 | Almond et al. | 604/167.06 |
| 7,758,501 B2* | 7/2010 | Frasier et al. | 600/233 |
| 7,780,594 B2* | 8/2010 | Hutton | 600/219 |
| 7,850,608 B2* | 12/2010 | Hamada | 600/219 |
| 7,892,174 B2* | 2/2011 | Hestad et al. | 600/214 |
| 7,931,589 B2* | 4/2011 | Cohen et al. | 600/210 |
| 7,935,053 B2* | 5/2011 | Karpowicz et al. | 600/224 |
| 7,981,031 B2* | 7/2011 | Frasier et al. | 600/224 |
| 7,985,179 B2* | 7/2011 | Gephart et al. | 600/224 |
| 8,038,611 B2* | 10/2011 | Raymond et al. | 600/231 |
| 8,062,217 B2* | 11/2011 | Boucher et al. | 600/210 |
| 8,075,482 B2* | 12/2011 | Beckman | A61B 17/3423 600/208 |
| 8,083,673 B2* | 12/2011 | Rosen | 600/224 |
| 8,105,236 B2* | 1/2012 | Malandain et al. | 600/219 |
| 8,152,721 B2* | 4/2012 | Michaeli et al. | 600/224 |
| 8,182,519 B2* | 5/2012 | Loftus et al. | 606/301 |
| 8,192,463 B2* | 6/2012 | McLoughlin | 606/233 |
| 8,211,012 B2* | 7/2012 | Wing et al. | 600/215 |
| 8,262,570 B2* | 9/2012 | White et al. | 600/219 |
| 8,267,859 B2* | 9/2012 | Holmes | 600/213 |
| 8,303,499 B2* | 11/2012 | Hamada | 600/233 |
| 8,317,692 B2* | 11/2012 | Loftus et al. | 600/210 |
| 8,353,826 B2* | 1/2013 | Weiman | 600/219 |
| 2001/0041828 A1* | 11/2001 | Deckman et al. | 600/232 |
| 2002/0072713 A1* | 6/2002 | Almond et al. | 604/167.05 |
| 2003/0088157 A1* | 5/2003 | Vassiliades et al. | 600/202 |
| 2004/0087833 A1* | 5/2004 | Bauer et al. | 600/201 |
| 2004/0176665 A1* | 9/2004 | Branch et al. | 600/210 |
| 2005/0070765 A1* | 3/2005 | Abdelgany et al. | 600/214 |
| 2005/0080320 A1* | 4/2005 | Lee | A61B 17/02 600/214 |
| 2005/0159651 A1* | 7/2005 | Raymond et al. | 600/213 |
| 2005/0165281 A1* | 7/2005 | Ravikumar | A61B 17/02 600/204 |
| 2005/0203347 A1* | 9/2005 | Fehling | 600/210 |
| 2005/0215866 A1* | 9/2005 | Kim | 600/233 |
| 2005/0277812 A1* | 12/2005 | Myles | 600/231 |
| 2006/0052672 A1* | 3/2006 | Landry et al. | 600/233 |
| 2006/0142643 A1* | 6/2006 | Parker | 600/219 |
| 2006/0178566 A1* | 8/2006 | Fetzer | 600/234 |
| 2007/0010716 A1* | 1/2007 | Malandain et al. | 600/224 |
| 2007/0038033 A1* | 2/2007 | Jones et al. | 600/219 |
| 2007/0156024 A1* | 7/2007 | Frasier et al. | 600/219 |
| 2007/0156025 A1* | 7/2007 | Marchek et al. | 600/224 |
| 2007/0156026 A1* | 7/2007 | Frasier et al. | 600/224 |
| 2007/0203399 A1* | 8/2007 | Gephart | A61B 1/32 600/219 |
| 2007/0238932 A1* | 10/2007 | Jones et al. | 600/224 |
| 2007/0282171 A1* | 12/2007 | Karpowicz et al. | 600/224 |
| 2008/0183046 A1* | 7/2008 | Boucher et al. | 600/232 |
| 2008/0319268 A1* | 12/2008 | Michaeli et al. | 600/202 |
| 2009/0018400 A1* | 1/2009 | Raymond et al. | 600/224 |
| 2009/0018401 A1* | 1/2009 | Kim | 600/231 |
| 2009/0069635 A1* | 3/2009 | Gephart et al. | 600/224 |
| 2009/0124861 A1* | 5/2009 | Fetzer | 600/226 |
| 2009/0158674 A1* | 6/2009 | Guerrero et al. | 52/81.2 |
| 2010/0069740 A1 | 3/2010 | Larson et al. | |
| 2010/0081885 A1* | 4/2010 | Wing et al. | 600/215 |
| 2010/0160947 A1 | 6/2010 | Akyuz et al. | |
| 2010/0274094 A1* | 10/2010 | Abdelgany | A61B 17/0293 600/207 |
| 2011/0004067 A1* | 1/2011 | Marchek et al. | 600/214 |
| 2011/0224496 A1* | 9/2011 | Weiman | 600/219 |
| 2011/0224497 A1* | 9/2011 | Weiman et al. | 600/231 |
| 2011/0237898 A1 | 9/2011 | Stone et al. | |
| 2011/0245621 A1* | 10/2011 | Frasier et al. | 600/233 |
| 2011/0301421 A1* | 12/2011 | Michaeli | A61B 17/0293 600/211 |
| 2011/0301423 A1* | 12/2011 | Koros et al. | 600/229 |
| 2011/0313256 A1* | 12/2011 | Raymond et al. | 600/231 |
| 2012/0046527 A1* | 2/2012 | Cianfrani et al. | 600/232 |
| 2012/0101341 A1* | 4/2012 | Malandain et al. | 600/204 |
| 2012/0165613 A1* | 6/2012 | Loftus et al. | 600/210 |
| 2012/0172669 A1* | 7/2012 | Loftus et al. | 600/210 |
| 2012/0172670 A1* | 7/2012 | Hamada | 600/219 |
| 2012/0190935 A1* | 7/2012 | Loftus et al. | 600/227 |
| 2012/0245432 A1* | 9/2012 | Karpowicz et al. | 600/224 |
| 2013/0066161 A1* | 3/2013 | Wenchell | 600/208 |

OTHER PUBLICATIONS

International Search Report and Written Opinion, PCT/US2014/055681, dated Dec. 16, 2014, 8 pages.

* cited by examiner

RETRACTOR DEVICE AND METHOD

CROSS-REFERENCE TO RELATED APPLICATION

This application is a continuation-in-part of U.S. application Ser. No. 13/659,673, filed on Oct. 24, 2012, which is incorporated by reference in its entirety.

TECHNICAL FIELD

The present disclosure generally relates to the field of orthopedics and spinal surgery, and more particularly, to retractor devices for use in surgery. Related methods are also described.

BACKGROUND

In the treatment of diseases, injuries or malformations affecting spinal motion segments, and especially those affecting disc tissue, it has long been known to remove some or all of a degenerated, ruptured or otherwise failing disc. In cases involving intervertebral disc tissue that has been removed or is otherwise absent from a spinal motion segment, corrective measures are taken to ensure the proper spacing of the vertebrae formerly separated by the removed disc tissue.

Such corrective measures may include spinal fusion or insertion of a disc prosthesis into the disc space. Such surgical techniques require access to the surgical site through tissue. Invasive techniques may cause tissue necrosis and creep. Accordingly, devices and methods for reducing invasiveness associated with accessing a spinal surgical site are desired.

BRIEF SUMMARY

The present disclosure generally relates to a retractor device for tissue retraction. In one embodiment, the retractor device includes a ring disposed within a frame. A plurality of arm assemblies with corresponding retractor blades are operatively coupled to the ring and fixedly coupled to the frame such that actuation of the ring causes actuation of the arm assemblies (and therefore, blades) from a first position to a second position. The blades may be removably attached to the arm assemblies such that the blades can be replaced while the device is in use. Further, an actuator may be used to engage the retractor device to cause circumferential movement of the ring, and a ratcheting mechanism may be used to provide for one-way rotation of the rings. The device may further include a release mechanism for enabling the arm assemblies and blades to move from the second position back to the first position or another position.

In some embodiments, a retractor device according to the present disclosure may take the form of a dual stage retractor and include a pair of rings and a pair of corresponding gears disposed within a frame. The retractor device includes a plurality of arm assemblies with corresponding retractor blades operatively coupled to the rings and fixedly coupled to the frame such that actuation of the rings causes actuation of the arm assemblies (and therefore, blades) from a first position to a second position. The arm assemblies are preferably configured such that opposing arm assemblies are coupled to the same ring and adjacent arm assemblies are coupled to different rings. In this manner, the retractor device provides for dual stage retraction in which different pairs of arm assemblies are operated independently, thus providing for staged actuation of different pairs of blades. The blades may be removably attached to the arm assemblies such that the blades can be replaced while the device is in use. Further, an actuator may be used to engage the retractor device to cause circumferential movement of the rings, and ratcheting mechanisms may be used to provide for one-way rotation of the rings. The device may further include a pair of release mechanisms for enabling the arm assemblies and blades to move from the second position back to the first position or another position.

Related methods for using the retractor devices according to the present disclosure are also described.

BRIEF DESCRIPTION OF THE DRAWINGS

Reference is now made to the following descriptions taken in conjunction with the accompanying drawings.

DETAILED DESCRIPTION

Various embodiments of a retractor device and methods of using such retractor devices according to the present disclosure are described. It is to be understood, however, that the following explanation is merely exemplary in describing the devices and methods of the present disclosure. Accordingly, several modifications, changes and substitutions are contemplated.

Figure 1A:
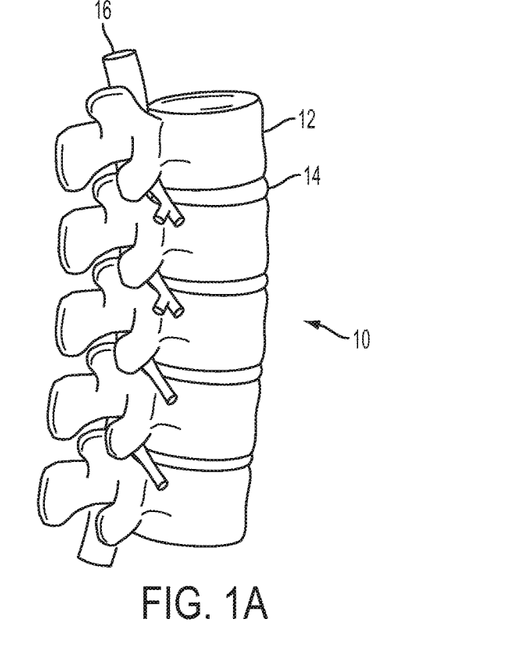
FIG. 1A illustrates a portion of a human spinal column.
Figure 1B:
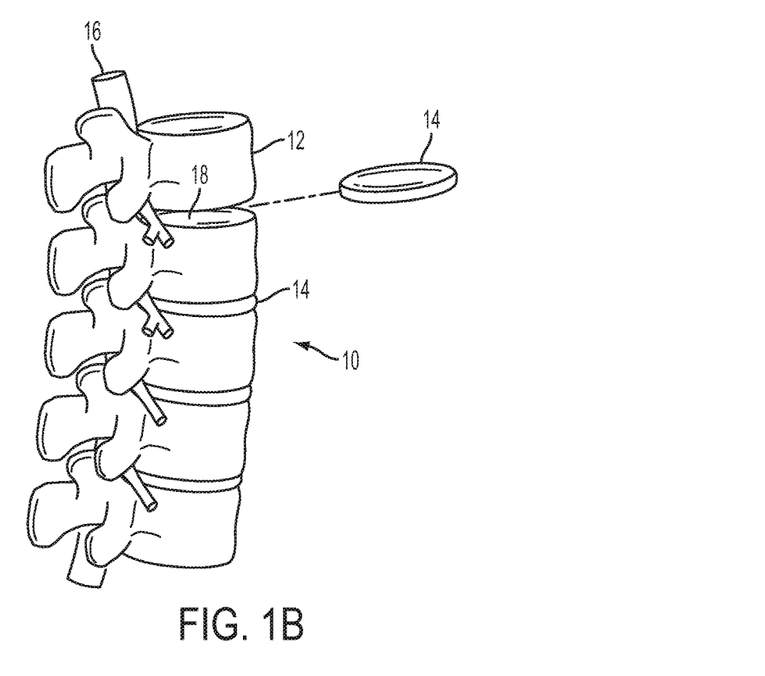
FIG. 1B illustrates a portion of a human spinal column with an intervertebral disc removed.

A portion of a human spinal column 10 is schematically illustrated in FIG. 1A and includes a series of vertebrae 12 intersected by a series of intervertebral discs 14. The vertebrae 12 generally encapsulate a spinal cord 16, which generally comprises nervous tissue and serves as the main pathway for information connecting the brain and peripheral nervous system. Referring to FIG. 1B, it sometimes becomes necessary to remove a diseased, or otherwise failing, intervertebral disc. Such procedures leave an intervertebral disc space 18 defined between adjacent vertebrae of the spinal column. Some surgical procedures call for fusion of the adjacent vertebrae 12, while other procedures may call for insertion of a prosthetic disc into the intervertebral disc space 18. In either scenario, or in additional spinal surgery scenarios, access to the intervertebral disc space 18 through tissue is required. According to the principles of the present disclosure, it is desirable to provide for minimally invasive access to the surgical site through such tissue.

The retractor devices described herein are preferably used in surgical procedures involving the cervical and/or lumbar regions of the spinal column; however, the retractor devices described herein may be used in other surgical applications requiring distraction of tissue and such uses are contemplated as falling within the scope of the present disclosure.

A retractor device 20 according to some embodiments of the present disclosure is illustrated in FIGS. 2-5. The retractor device 20 includes a frame 22, which has a ring 24 at least partially disposed within the frame. The retractor device 20 further includes a plurality of arm members 26, which are operatively coupled to the ring 24 and fixedly coupled to the frame 22. To facilitate coupling of the arm members to the frame, connectors 28, such as pins or the like, may be used to secure the arm members 26 to the frame, while allowing pivoting of the arm members about the connectors. Such an arrangement facilitates opening and closing of the arm members 26 as will be described.

The retractor device 20 further includes a plurality of blade members 32, which may be removably coupled to the arm members 26. To facilitate such coupling, and with particular reference to FIG. 3, the arm members 26 may include a flange portion 34, which includes a threaded aperture 36 defined therein. A connector 38, such as the illustrated set screw, may then be used to secure the blade member 32 to the flange portion 34 of the arm member 26 by passing a threaded end of the connector through the blade member and into threaded engagement with the flange portion via the threaded aperture 36.

In some embodiments, opposing pairs of arm members are of substantially equal length, while adjacent pairs of arm members of different length. For example, as illustrated in FIGS. 2-5, a first set of opposing arm members 26 have substantially the same length, while the other set of opposing arm members 26 have substantially the same length, which is greater than the length of the first set of opposing arm members 26. That is, pairs of adjacent arm members 26 may have different lengths, while opposing pairs of arm members 26 may have substantially the same length. In this manner, the retractor device 20 may be actuated to achieve non-uniform retraction (e.g., oblong retraction) of tissue to thereby lessen the strain on such tissue during use. Of course, in other embodiments, the arm members may be of substantially equal length to achieve uniform retraction.

The arm members 26 are adapted for coupling to the ring 24 via an elongated slot 40, which is adapted to receive a mounting post 42 extending axially from the ring. To accommodate the mounting posts 42, the ring 24 may include a plurality of protrusions 44, which extend inwardly of the remaining portion of the ring. In some embodiments, the mounting post 42 may be substantially cylindrical in shape, however, other configurations are contemplated so long as the mounting post fits within and is adapted for moving along the elongated slot 40 as will be described.

Figure 2:
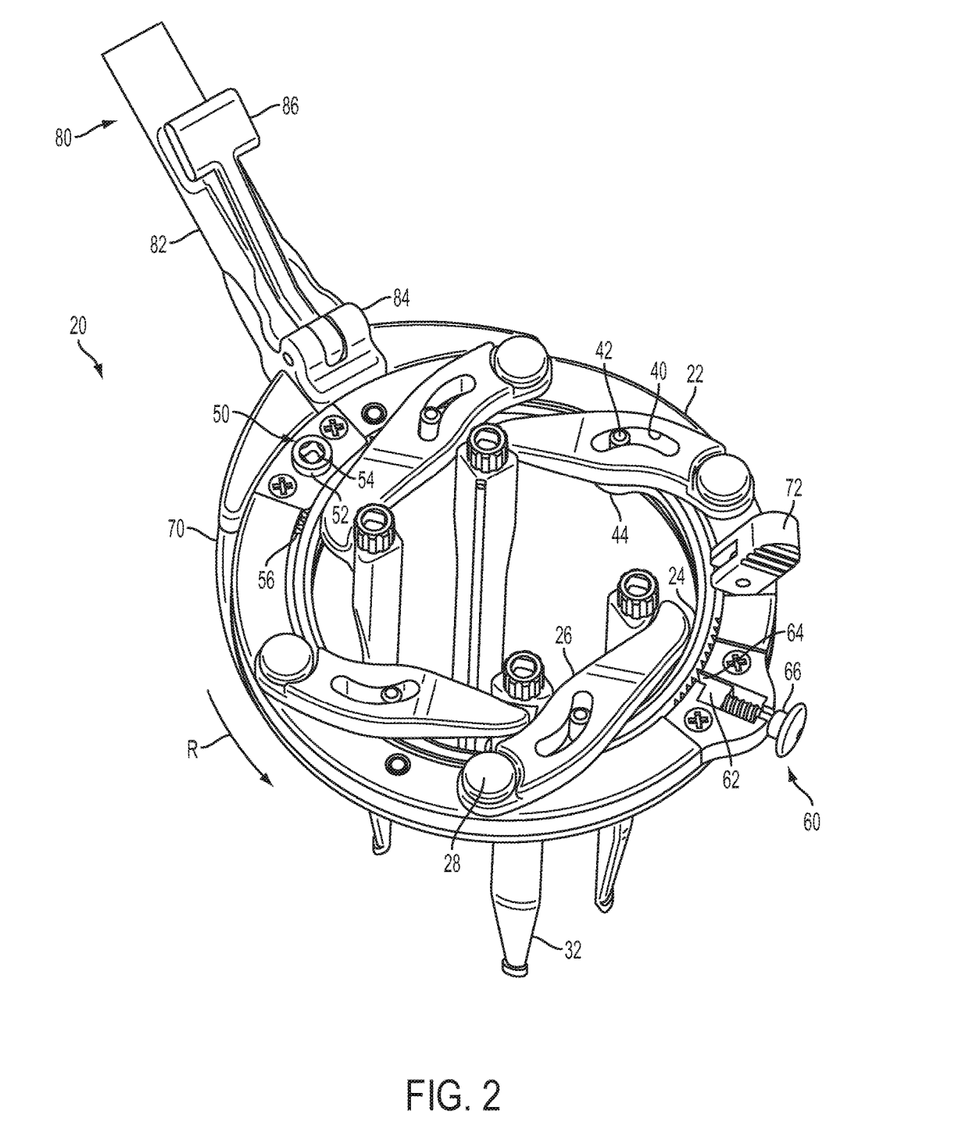
FIG. 2 illustrates a top perspective view of a retractor device with bladed in an open position according to one embodiment of the present disclosure.
Figure 3:
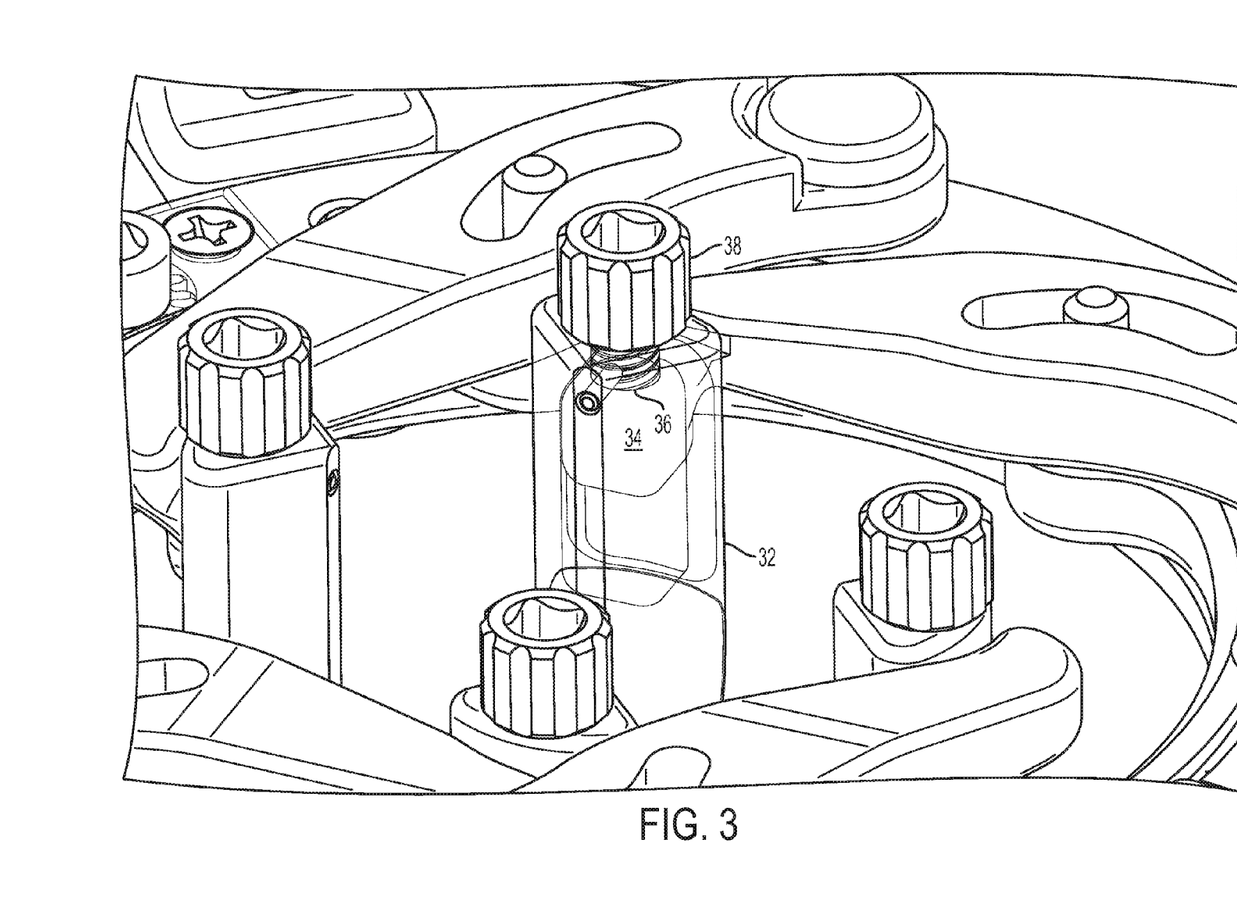
FIG. 3 illustrates a detailed perspective view of a portion of the retractor device of FIG. 2 with a broken-away view of an embodiment of an interconnection of a retractor blade with a retractor arm.
Figure 4:
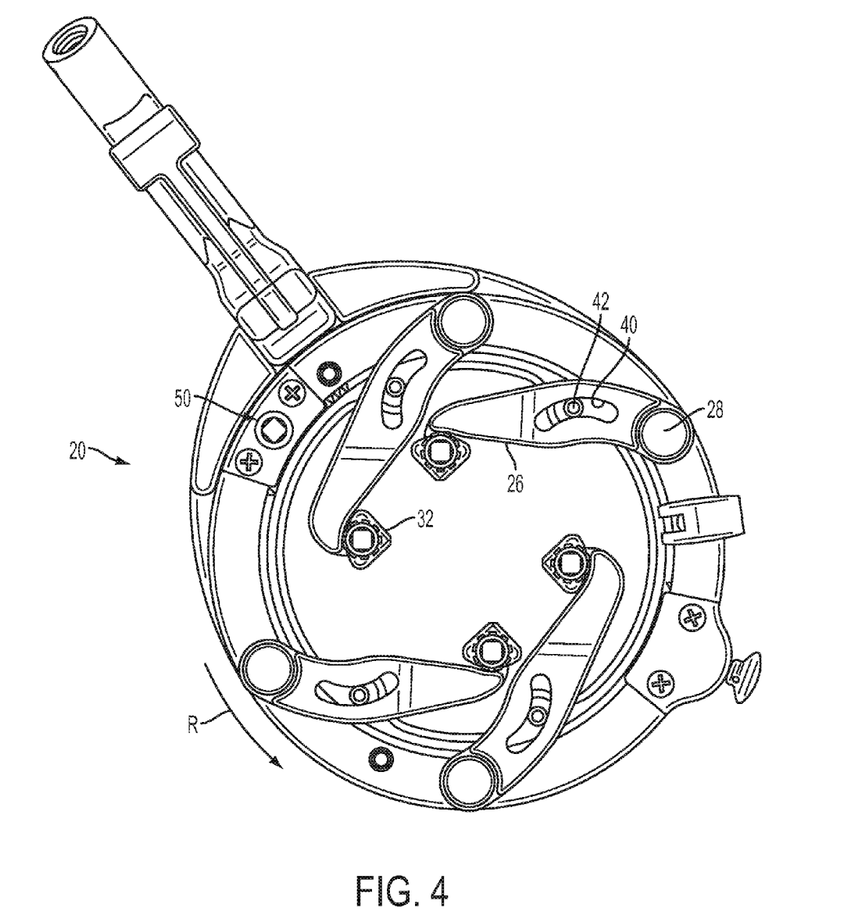
FIG. 4 illustrates a top view of the retractor device of FIG. 2 with the blades in a partially open position.
Figure 5:
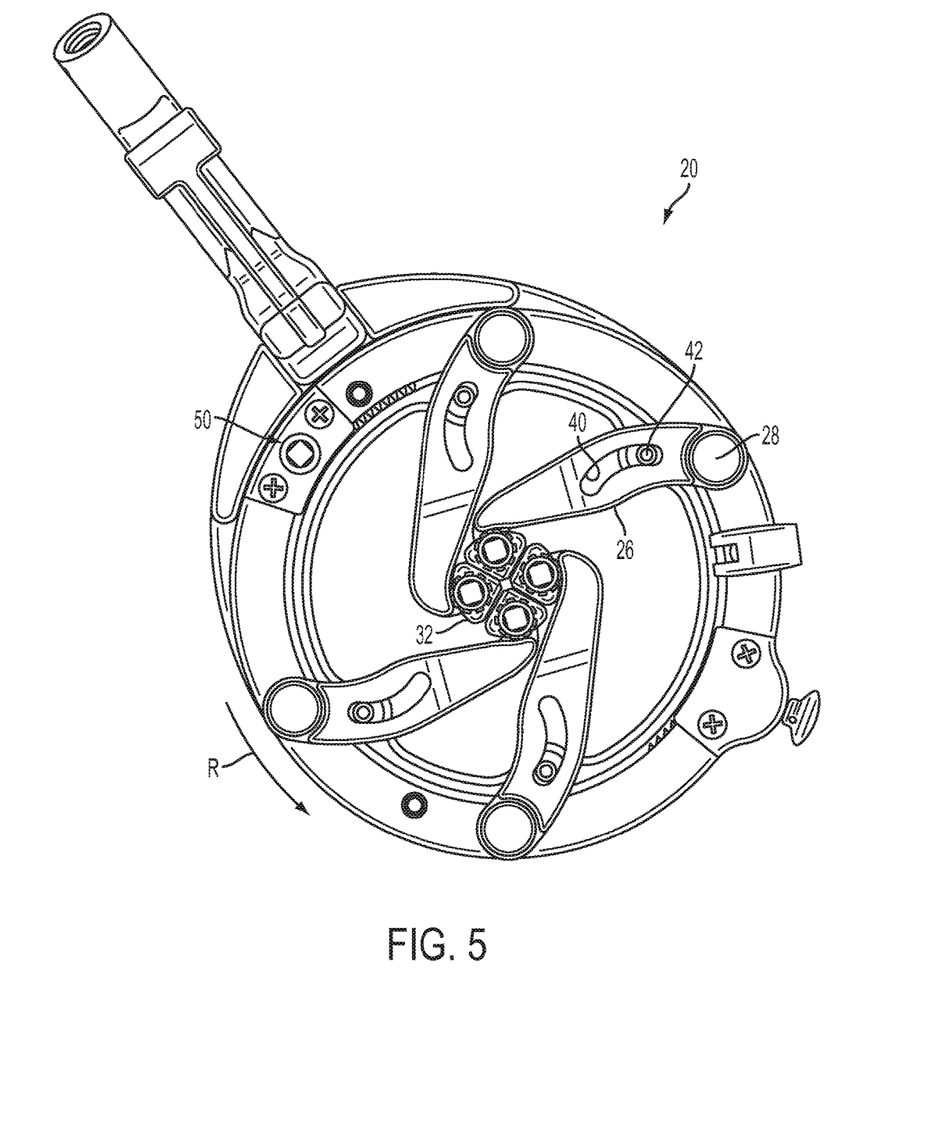
FIG. 5 illustrates a top view of the retractor device of FIG. 2 with the blades in a closed position.

Referring to FIGS. 2, 4 and 5, the arms 26 (and thus the blades 32) are movable from a substantially closed position (FIG. 5), to an intermediate position (FIG. 4), and to a substantially open position (FIG. 3). Accordingly, the retractor device 20 may be inserted through a relatively small incision site and then later may be actuated to allow access to the operation site. To facilitate such movement, the retractor device 20 includes an actuator 50 that, in some embodiments, includes a head member 52 operatively coupled to a drive gear (not shown) for driving the ring 24. The head member 52 may include a recessed portion 54 of hexagonal configuration for receiving a correspondingly shaped driver (not shown). Of course, other configurations other than a hexagonal configuration are contemplated so long as the configurations of the head member 52 and tool are complementary. The drive gear is coupled to corresponding teeth 56 disposed along a circumference of the ring 24.

In practice, the actuator 50 is engaged with a tool and rotated via rotation of the head member 52. The teeth of the drive gear thus engage the teeth 56 of the ring 24 to thereby urge the ring in a direction of rotation opposite that of the drive gear. Rotation of the ring 24 in the direction R (shown in FIGS. 2, 4 and 5) causes translation of the mounting post 42 along the elongated slot 40 to thereby move the blade members 32 from the closed position of FIG. 5 to the open position of FIG. 2. In some embodiments, rotation is only desired in one direction such that the surrounding tissue does not urge the blade members 32 back to the closed position of FIG. 5. Accordingly, with reference to FIG. 2, a portion of the frame 22 is broken away to illustrate a ratchet assembly 60, which accommodates one-way rotation of the ring 24 (and therefore blade members 32) such that the surrounding tissue does not urge the blades 32 back to the closed position of FIG. 5. The ratchet assembly 60 may include a ratchet body 62 having a flange portion 64 extending into the teeth 56 of the ring 24. In this manner, the flange portion 64 of the ratchet assembly 60 cooperates with the contour of the teeth 56 to permit rotation in the desired direction of rotation R when opening the blade members 32, while preventing rotation in a direction opposite to R. A locking member 66, such as a screw, may be used to maintain the ratchet body 62 in place during use, while also providing a mechanism for loosening the ratchet body to allow for movement of the blade members 32 back to the closed position of FIG. 2 when access through the surgical site is no longer needed.

Continuing with reference to FIG. 2, the retractor device 20 may optionally be used with a support member 70, which may take the form of a support ring that extends beneath and about the frame 22. The support member 70 is adapted to rotate relative to the retractor device 20. Upon desired positioning, the support member 70 may be secured to the retractor device 20 via locking member 72, which may be actuated to engage and grip the retractor device.

The support member 70 may be used to facilitate coupling of the retractor device 20 to operating room equipment, such as an operation stand (not shown). Accordingly, a coupling member 80 may be provided for engaging the support member to thereby couple the retractor device 20 to such equipment. In one embodiment, the coupling member 80 includes a rod 82 having an attachment portion 84 for coupling the rod to the support member 70. The coupling member 80 may further include a latch 86 for facilitating removal of the coupling member from the support member 70.

Figure 6:
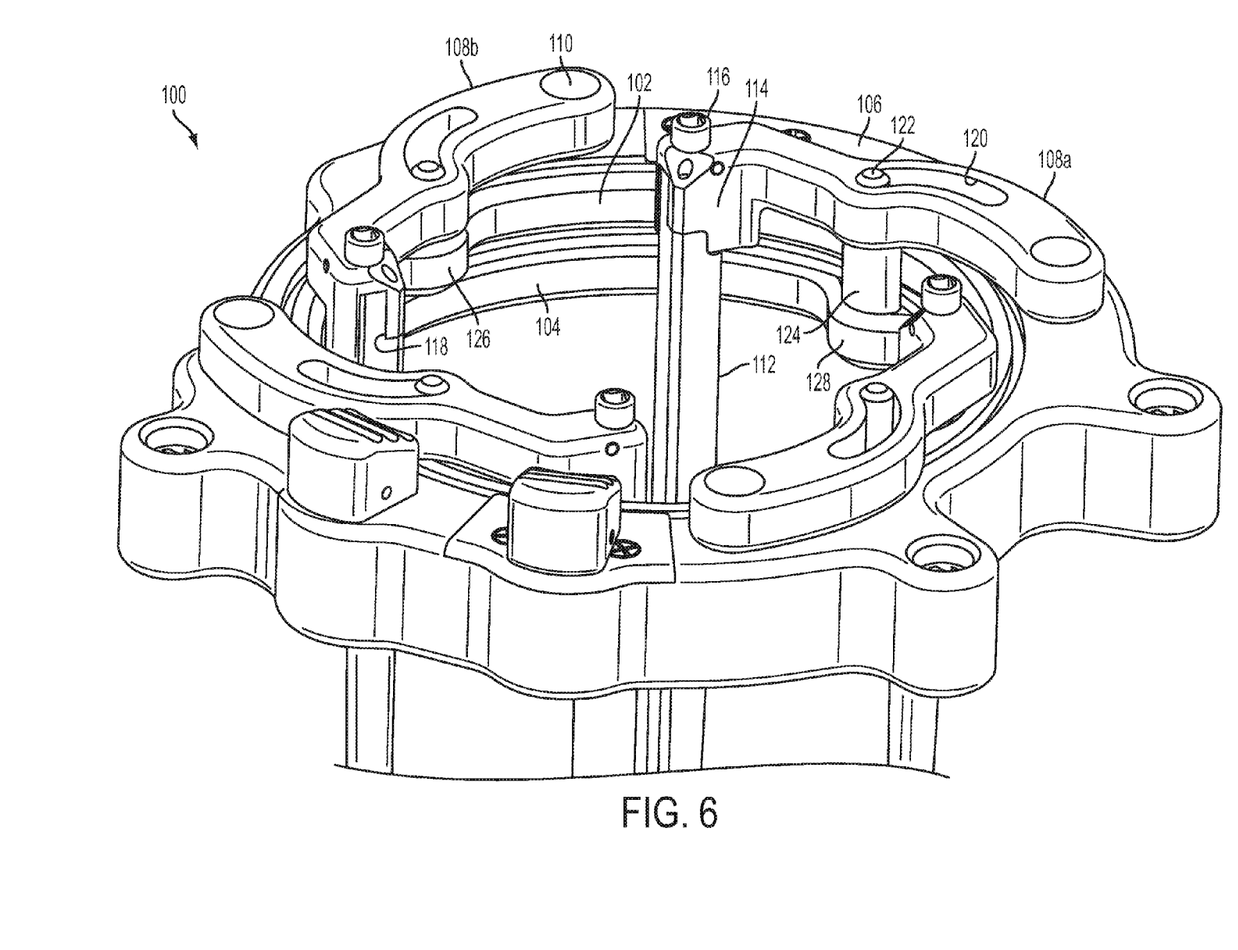
FIG. 6 illustrates a top perspective view of a retractor device with blades in an open position according to another embodiment of the present disclosure.
Figure 7:
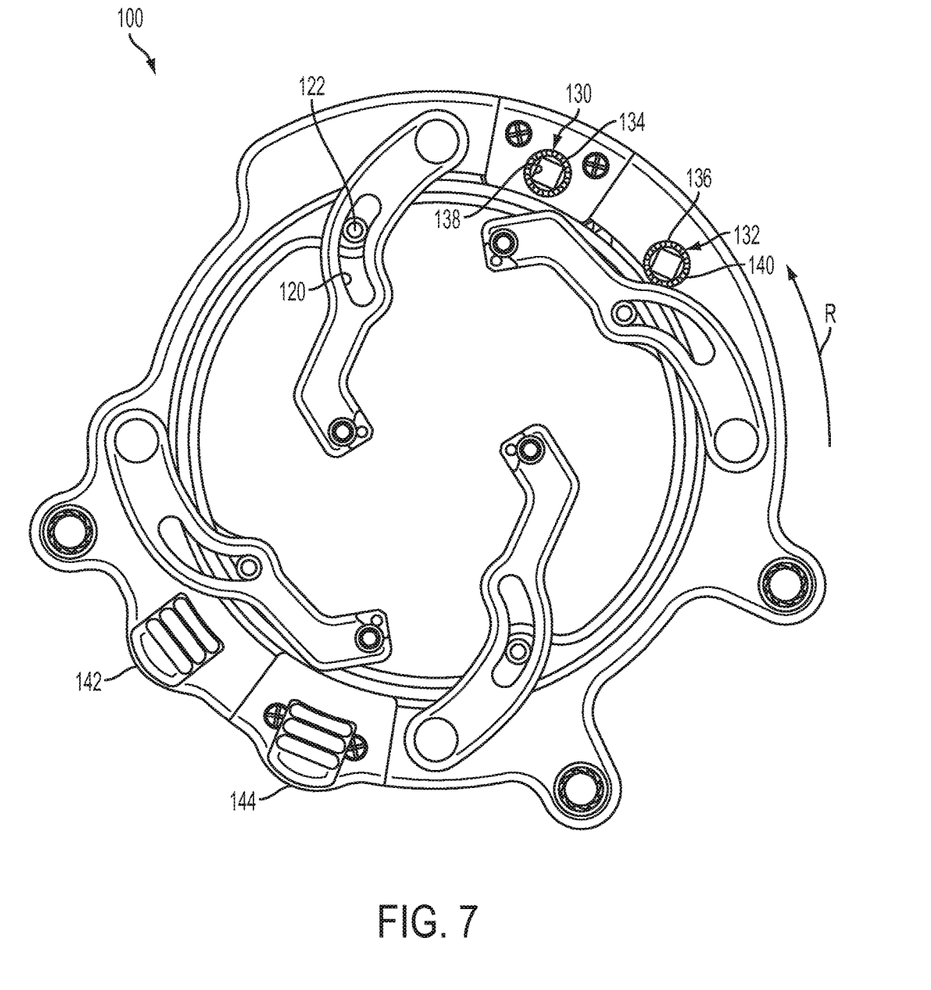
FIG. 7 illustrates a top view of the retractor device of FIG. 6 with the blades in a partially open position.
Figure 8:
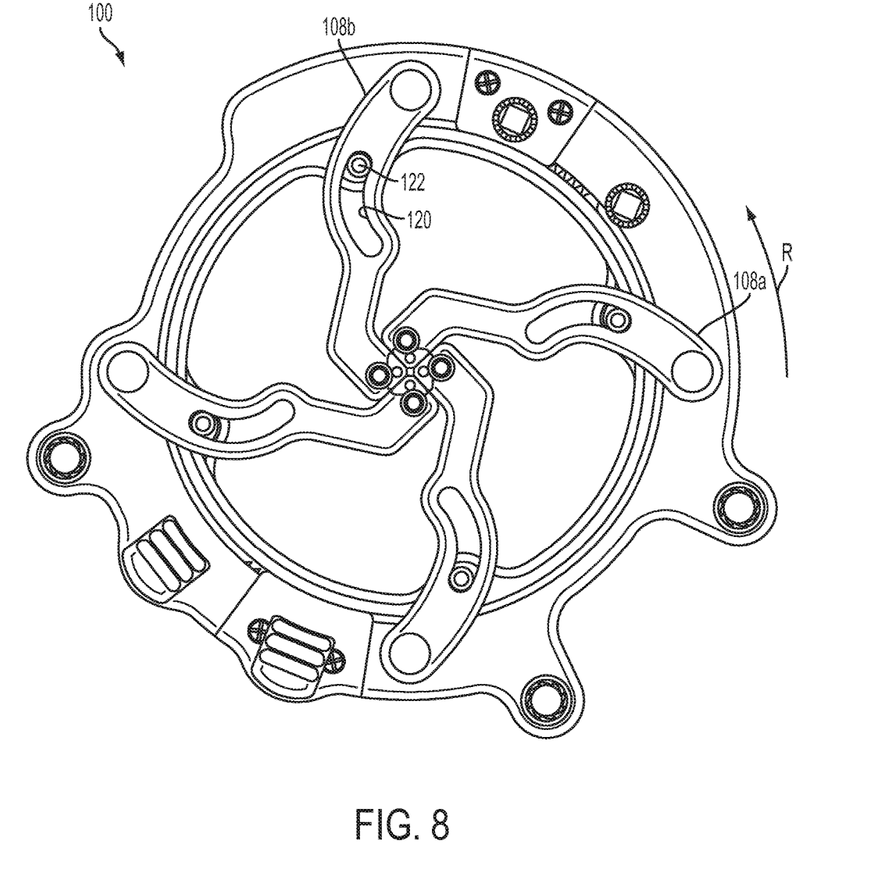
FIG. 8 illustrates a top view of the retractor device of FIG. 6 with the blades in a closed position.

FIGS. 6-8 illustrate an alternative retractor device 100 according to the principles of the present disclosure. The retractor device 100 includes an upper ring 102 and a lower ring 104 disposed at least partially within a frame 106. The retractor device 100 further includes a plurality of arm members 108, which are operatively coupled to one of the upper and lower rings 102, 104 and fixedly coupled to the frame 106. To facilitate coupling of the arm members 108 to the frame 106, connectors 110, such as pins or the like, may be used to secure the arm members to the frame, while allowing pivoting of the arm members about the connectors. Such an arrangement facilitates opening and closing of the arm members 108 as will be described.

The retractor device 100 further includes a plurality of blade members 112, which may be removably coupled to the arm members 108. To facilitate such coupling, and with particular reference to FIG. 6, the arm members 108 may include a flange portion 114, which includes a threaded aperture defined therein. A connector 116, such as the illustrated set screw, may then be used to secure the blade member 112 to the flange portion 114 of the arm member 108 by passing a threaded end of the connector through the flange portion and into threaded engagement with the blade member. To accommodate alignment, the flange portion 114 defines an opening or recess 118 into which an upper end of the blade member 112 is positioned. Such an arrangement prevents undesired lateral deviations of the blade member 112 as it extends in a direction away from the frame 106.

The arm members 108 are adapted for coupling to one of the upper and lower rings 102, 104 via an elongated slot 120, which is adapted to receive a mounting post 122 extending from one of the upper and lower rings. In one embodiment, opposing arm members 108 are coupled to the same ring and adjacent arm members are coupled to different rings. For example, with particular reference to FIG. 6, the arm member designated 108a is coupled to the lower ring 104, while the adjacent arm member designated 108b is coupled to the upper ring 102. As each of the arm members 108 lie generally in the same plane, the arm member 108a is coupled to the lower ring 104 via the mounting post 122 and a support base 124 extending from the lower ring. The support base 124 preferably has an increased width relative to the mounting post 122 to thereby provide support for the arm member 108a. The arm member 108b, on the other hand, is coupled to the upper ring 102 via the mounting post 122, which extends from the upper ring.

To accommodate the mounting posts 122 and the support bases 124, the upper and lower rings 102, 104 may include a plurality of respective protrusions 126, 128 which extend inwardly of the remaining portions of the rings. In some embodiments, the mounting posts 122 may be substantially cylindrical in shape, however, other configurations are contemplated so long as the mounting post fits within and is adapted for moving along the elongated slot 120 as will be described.

Provision of the upper and lower rings 102, 104 allows for dual-stage movement of the arm members 108. That is, a pair of opposing arm members 108 may be actuated independently from the other pair of opposing arm members such that the blade members are movable from a substantially closed position (FIG. 8), to an intermediate position (FIG. 7), and to a substantially open position (FIG. 6) in a staged manner. In one embodiment, the blade members 112 may be opened from between 10-60 mm in diameter, thus providing the opportunity to achieve a wide expansion range, while providing the ability to penetrate through a small incision of 10 mm. Of course, the retractor device 100 may be designed to achieve alternative expansion ranges.

Given the staged operation of the retractor device 100, the arm members 108 may be of substantially the same length as staged actuation of the arm members allows for non-uniform retraction (e.g., oblong retraction), which may be desirable in circumstances where excessive tissue strain is an issue. In other embodiments, the retractor device 100 may be actuated to achieve uniform retraction.

To facilitate movement of the arm members 108 (and therefore blade members 112), and with particular reference to FIGS. 7 and 8, the retractor device 100 includes a pair of actuators 130, 132 that, in some embodiments, include respective head members 134, 136 operatively coupled to drive gears (not shown) for driving the upper and lower rings 102, 104, respectively. The head members 134, 136 may include respective recessed portions 138, 140 of hexagonal configuration for receiving a correspondingly shaped driver (not shown). Of course, other configurations other than a hexagonal configuration are contemplated so long as the configurations of the head members 134, 136 and tool are complementary. The drive gear is coupled to corresponding teeth disposed along a circumference of the upper and lower rings 102, 104. The head member 136 associated with lower ring 104 may include a rod-like intermediate member (not shown) between the head member and drive gear so as to not engage or otherwise disrupt rotation of the upper ring 102.

In practice, the actuators 130, 132 are engaged with a tool and rotated via rotation of the respective head members 134, 136. Such engagement and actuation may occur simultaneously or intermittently. When actuated, the teeth of the drive gear engage the teeth of the corresponding upper or lower ring 102, 104 to thereby urge the upper or lower ring in a direction of rotation opposite that of the drive gear. Rotation of the upper and lower rings 102, 104 in the direction R (shown in FIGS. 7 and 8) causes translation of the mounting posts 122 along the elongated slots 120 to thereby move the blade members 112 from the closed position of FIG. 8 to the open position of FIG. 6. In some embodiments, rotation is only desired in one direction such that the surrounding tissue does not urge the blade members 112 back to the closed position of FIG. 8. Accordingly, the retractor device 100 may include a pair of ratchet devices (not shown), which cooperate with the contour of the teeth of the respective upper and lower rings to permit rotation in the desired direction of rotation R when opening the blade members 112, while preventing rotation in a direction opposite to R. The ratchet devices may be operatively coupled to respective release buttons 142, 144, which when engaged, act to release ratchet devices from the respective upper and lower rings to thereby permit closure of the blade members 112. Support and coupling members similar to those described with respect to FIGS. 2-5 may also be used with the retractor device 100.

To facilitate use of the embodiments of the retractor devices 20, 100 disclosed herein, the arm members 26, 108 and blade members 32, 112 may be formed of, or modified to include, a radiopaque material. In other embodiments, the arm members 26, 108 may be formed of a radiolucent material.

While various embodiments of a retractor device and related methods of using such devices have been described above, it should be understood that they have been presented by way of example only, and not limitation. For example, while only four arm members (and corresponding blade members) are shown in the embodiments disclosed herein, it is to be appreciated that there may be more or less pairs of arm members to achieve retraction. Moreover, in the embodiments described with respect to FIGS. 6-8, should additional pairs of arm and blade members be used, additional sets of corresponding rings and gears may be added to the retractor device 100. Thus, the breadth and scope of the present disclosure should not be limited by any of the above-described exemplary embodiments, but should be defined only in accordance with the following claims and their equivalents. Moreover, the above advantages and features are provided in described embodiments, but shall not limit the application of the claims to processes and structures accomplishing any or all of the above advantages.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Technical Field," the claims should not be limited by the language chosen under this heading to describe the so-called technical field. Further, a description of a technology in the "Background" is not to be construed as an admission that technology is prior art to any invention(s) in this disclosure. Neither is the "Brief Summary" to be considered as a characterization of the invention(s) set forth in the claims found herein. Furthermore, any reference in this disclosure to "invention" in the singular should not be used to argue that there is only a single point of novelty claimed in this disclosure. Multiple inventions may be set forth according to the limitations of the multiple claims associated with this disclosure, and the claims accordingly define the invention(s), and their equivalents, that are protected thereby. In all instances, the scope of the claims shall be considered on their own merits in light of the specification, but should not be constrained by the headings set forth herein.

What is claimed is:

1. A retractor device, comprising:
   a frame;
   a ring disposed at least partially within the frame, the ring having a plurality of mounting posts fixedly and directly connected to the ring and extending axially from the ring;
   a plurality of arm members coupled to the frame and respectively operatively coupled to the ring via the mounting posts, a first of the arm members having a first length, and a second of the arm members having a second length greater than the first length; and
   an actuator for imparting rotation to the ring to thereby impart movement to the arm members operatively coupled to the ring, wherein
   each of the arm members includes an elongated and arcuate slot defined therethrough, and
   the mounting posts are respectively disposed in the slots.

2. A retractor device according to claim 1, wherein the ring includes a plurality of teeth along a circumferential edge of the ring, and the actuator includes a gear that engages the teeth of the ring.

3. A retractor device according to claim 2, wherein an axis of rotation of the gear is substantially parallel with an axis of rotation of the ring.

4. A retractor device according to claim 2, further comprising a ratchet assembly having a flange portion that engages the teeth of the ring during rotation of the ring.

5. A retractor device according to claim 2, wherein rotation of the actuator causes both the first of the arm members and the second of the arm members to translate.

6. A retractor device according to claim 1, wherein the ring further comprises a plurality of radially inward protrusions, the plurality of mounting posts extending axially from respective protrusions.

7. A retractor device according to claim 1, further comprising a blade member coupled to and extending from at least one arm member.

8. A retractor device according to claim 7, wherein the arm member comprises a flange portion extending from the arm member, the flange portion having a threaded aperture defined therein.

9. A retractor device according to claim 8, wherein an upper portion of the blade member is disposed over the flange portion, and a connector is disposed through the upper portion of the blade member and into the threaded aperture of the flange portion to thereby secure the blade member to the arm member.

10. A retractor device according to claim 1, further comprising a support member disposed about the frame.

11. A retractor device according to claim 1, wherein
   the ring includes a plurality of teeth along a circumferential edge of the ring, and
   the actuator including a gear that engages the teeth of the ring.

12. A retractor device according to claim 11, wherein an axis of rotation of the gear is substantially parallel with an axis of rotation of the ring.

13. A retractor device according to claim 11, wherein the ring further comprises a plurality of radially inward protrusions, the plurality of mounting posts extending axially from respective protrusions.

14. A retractor device according to claim 11, further comprising blade members coupled to and extending from respective arm members.

15. A retractor device according to claim 1, wherein the mounting posts are integrally formed with the ring such that the ring and the mounting posts are provided as a single part.

16. A retractor device according to claim 1, wherein the ring includes a first ring and a second ring.

17. A retractor device according to claim 16, wherein the first arm member is coupled to the first ring, and the second arm member is coupled to the second ring.

18. A retractor device according to claim 17, wherein the first and second rings are rotatable independently such that a position of the first arm member and a position of the second arm member may be adjusted independently.

19. A retractor device according to claim 1, wherein the first of the arm members and the second of the arm members are operatively coupled to the same ring.

20. A retractor device according to claim 1, wherein the length of the first of the arm members is different than the length of the second of the arm members.

21. A method for using a retractor device, comprising:
   providing a retractor device having a frame and a ring disposed at least partially within the frame, the ring having a plurality of mounting posts fixedly and directly connected to the ring and extending axially therefrom, and the retractor device further having a plurality of arm members coupled to the frame and operatively coupled to the ring via the mounting posts, a first of the arm members having a first length, a second of the arm members having a second length greater than the first length, each of the arm members including an elongated and arcuate slot defined therethrough, and the mounting posts being respectively disposed in the slots;
   actuating the ring to impart movement to the arm members operatively coupled to the ring to impart an oblong retraction to a plurality of blade members disposed on the arm members.

22. A method according to claim 21, further comprising actuating the ring to cause translation of the mounting posts along the elongated slots.

23. A method according to claim 21, further comprising an actuator comprising a gear, and wherein the ring comprises teeth along a circumferential edge thereof, and further wherein the step of actuating the ring comprises actuating the gear to impart rotation to the ring.

24. A method according to claim 23, wherein actuating the gear causes rotation of the gear, the axis of rotation of the gear being substantially parallel to an axis of rotation of the ring.

25. A retractor device, comprising:
   a frame;
   a ring disposed at least partially within the frame, the ring having a mounting post fixedly and directly connected to the ring and extending in an axial direction from the ring;

an arm member coupled to the frame and operatively coupled to the ring via the mounting post;

a blade member coupled to and extending from the at least one arm member in the axial direction, the blade member including an aperture defined therein extending in the axial direction;

an actuator for imparting rotation to the ring to thereby impart movement to the arm member operatively coupled to the ring, wherein the arm member comprises a flange portion extending from the arm member, the flange portion having a threaded aperture defined therein and extending in the axial direction.

26. A retractor device according to claim 25, wherein the ring includes a plurality of teeth along a circumferential edge of the ring, and the actuator includes a gear that engages the teeth of the ring.

27. A retractor device according to claim 25, wherein the arm member includes an elongated slot defined therethrough, and the at least one mounting post is disposed within the elongated slot.

28. A retractor device according to claim 25, wherein an upper portion of the blade member is disposed over the flange portion, and a connector is disposed through an upper portion of the blade member and into the threaded aperture of the flange portion to thereby secure the blade member to the arm member.

* * * * *